(12) United States Patent
Nishino et al.

(10) Patent No.: US 6,825,317 B2
(45) Date of Patent: Nov. 30, 2004

(54) CYCLIC TETRAPEPTIDE DERIVATIVES AND PHARMACEUTICAL USES THEREOF

(75) Inventors: Norikazu Nishino, Fukuoka (JP); Minoru Yoshida, Saitama (JP); Sueharu Horinouchi, Tokyo (JP); Yasuhiko Komatsu, Saitama (JP)

(73) Assignee: Sumitomo Pharmaceuticals Company, Limited (JP)

( * ) Notice: Subject to any disclaimer, the term of this patent is extended or adjusted under 35 U.S.C. 154(b) by 420 days.

(21) Appl. No.: 09/945,237

(22) Filed: Aug. 31, 2001

(65) Prior Publication Data

US 2002/0120099 A1 Aug. 29, 2002

Related U.S. Application Data

(63) Continuation-in-part of application No. PCT/JP00/01141, filed on Feb. 28, 2000.

(30) Foreign Application Priority Data

Mar. 2, 1999 (JP) .......................................... 11-053851

(51) Int. Cl.[7] .............................................. C07K 7/52
(52) U.S. Cl. ...................... 530/317; 530/330; 530/331; 514/11; 424/9.363
(58) Field of Search ............................... 530/317, 330, 530/331; 514/11; 424/9.363

(56) References Cited

PUBLICATIONS

Nishino et al., "Cyclic Tetrapeptide Hydroxamic Acids Related to Trapoxin B Inhibit Histone Deacetylase", *Peptides*, pp. 832–833, 1998.
Tomizaki, et al., "Histone Deacetylase Inhibitors Based on Trapoxin B", *Peptide Science*, vol. 35, pp. 181–184, 1998.
Nishino, et al., "Synthesis of Cyclic Tetrapeptides Containing Non–natural Imino Acids", *Peptide Science*, vol. 35, pp. 189–192, 1998.
Tsukamoto, et al., "Synthesis and Activity of Cyl–1 Analogs having Hydroxamic Acid at Side Chain", *Peptide Science*, pp. 185–188, 1998.
Komatsu, et al., "Histone Deacetylase Inhibitors Up–regulate the Expression of Cell Surface MHC Class–I Molecules in B16/BL6 Cells", *Journal of Antibiotics*, vol. 51, No. 1, pp. 89–91, Jan., 1998.

Yoshida, et al., "Histone deacetylase as a new target for cancer chemotherapy", *Cancer Chemotherapy and Pharmacology* vol. 48, No. Suppl. 1, pp. S20–S26, Jul. 1, 2001.
Furuma, et al., "Potent histone deacetylase inhibitors built from trichostatin A and cyclic tetrapeptide antibiotics including trapoxin", *Proceedings of the National Academy of Sciences*, vol. 98, No. 1, pp. 87–92, Jan. 2, 2001.
International Search Report; PCT/JP00/01141; Apr. 21, 2000.
International Preliminary Examination Report; PCT/JP00/01141; Sep. 8, 2000.

*Primary Examiner*—Jon P. Weber
*Assistant Examiner*—David Lukton
(74) *Attorney, Agent, or Firm*—Fish & Richardson P.C.

(57) ABSTRACT

The present invention provides a cyclic tetrapeptide derivative represented by the following general formula (I) or a pharmaceutically acceptable salt thereof:

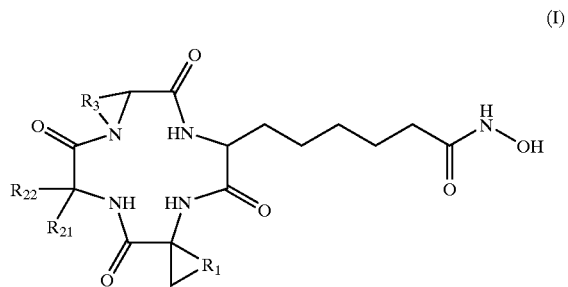

(I)

wherein
  each of $R_{21}$ and $R_{22}$ independently denotes hydrogen, a linear $C_1$–$C_6$-alkyl group to which a non-aromatic cycloalkyl group or an optionally substituted aromatic ring may be attached, or a branched $C_3$–$C_6$-alkyl group to which a non-aromatic cycloalkyl group or an optionally substituted aromatic ring may be attached; and
  each of $R_1$ and $R_3$ independently denotes a linear $C_1$–$C_5$-alkylene group which may have a $C_1$–$C_6$ side chain, in which the side chain may form a condensed ring structure on the alkylene chain.

The present invention also provides a histone deacetylase inhibitor, an MHC class-I molecule expression-promoting agent and a pharmaceutical composition, each of which comprises the above cyclic tetrapeptide derivative or pharmaceutically acceptable salt thereof as an active ingredient.

8 Claims, 2 Drawing Sheets

Acetylated lysine

Trapoxin A

Trapoxin B

Cyl-2

WF-3161

Chlamydocin

HC-toxin

SEQUENCE LISTING

<160> NUMBER OF SEQ ID NOS: 1

<210> SEQ ID NO 1
<211> LENGTH: 22
<212> TYPE: PRT
<213> ORGANISM: Artificial Sequence
<220> FEATURE:
<223> OTHER INFORMATION: A synthetic substrate peptide

<400> SEQUENCE: 1

Ser Gly Arg Gly Lys Gly Gly Lys Gly Leu Gly Lys Gly Gly Ala Lys
1               5                   10                  15

Arg His Arg Lys Val Cys
            20

CYCLIC TETRAPEPTIDE DERIVATIVES AND PHARMACEUTICAL USES THEREOF

RELATED APPLICATIONS

This application is a continuation in part and claims the benefit of priority under 35 U.S.C. §120 to Patent Convention Treaty (PCT) International Application Serial No: PCT/JP00/01141, filed on Feb. 28, 2000, which claims benefit of priority to JP 11/53851 1999, filed Mar. 2, 1999. The aforementioned applications are explicitly incorporated herein by reference in their entirety and for all purposes.

TECHNICAL FIELD

The present invention relates to novel cyclic tetrapeptide derivatives or pharmaceutically acceptable salts thereof, application of said compounds as histone deacetylase inhibitors and MHC class-I molecule expression-promoting agents, as well as pharmaceutical compositions that comprise said cyclic tetrapeptide derivatives or pharmaceutically acceptable salts thereof as active ingredients and which have utility as pharmaceuticals such as anti-cancer agents by taking advantage of the above histone deacetylase-inhibiting or MHC class-I molecule expression-promoting action.

BACKGROUND

An individual's own tissue cells express on their cell surface an MHC class-I molecule as an antigen presenting molecule to discriminate externally invading foreign matters and pathogens from themselves, in order to prevent false damage by their immunocytes. The immune system recognizes the MHC class-I molecule to identify the self tissue cells and eliminate them from the target of its attack. On the other hand, cancerized cells or cells infected with cancer viruses, which are originally self cells, differ from normal self cells in that they produce proteins associated with canceration or proteins derived from the cancer viruses, and antigens derived from these non-self proteins are presented by the MHC class-I molecule. The immunocytes, in particular cytotoxic T cells (CTLs), can recognize the non-self protein-derived antigens, thereby eliminating the cancer cells or cancer virus-infected cells.

It has been reported, however, that in certain kinds of cancer cells or cancer virus-infected cells, the expression of the MHC class-I molecule is reduced, so that the above elimination mechanism by the immune system is circumvented, causing expansion and enlargement of cancerized tissues as well as prolonged sustention and enlargement of cancer virus infection. In the studies for the purpose of preventing tumorization of the cancerized cells or cancer virus-infected cells, some results have been reported suggesting that therapeutic effects may be attained by recovery of the reduced expression of the MHC class-I molecule. For example, Tanaka et al. reported that in cancer cells transformed with adenovirus 12 or spontaneous melanoma, tumorization of these cancer cells disappeared upon enhancing the reduced expression of the MHC class-I molecule through introduction of MHC class-I gene; see, e.g., Tanaka, K., Isselbacher, K. J., Khoury, G. and Jay, G., Science, 228, 26–30, 1985; Tanaka, K., Gorelik, E., Watanabe, M., Hozumi, N. and Jay, G., Mol. Cell. Biol., 8, 1857–1861, 1988.

The expression of MHC class-I molecule occurs during the differentiation process after the growth of the self tissue cells, and the expression of MHC class-I molecule is expected to be enhanced by promoting the translation of endogenous proteins in this process. While there are several mechanisms that control the translation of endogenous proteins, one of those that may be considered to play an important role in gene expression is acetylation of histone proteins contained in the nuclear gene chromatins as their structural proteins. Illustratively, chromatin is composed of the basic unit referred to as a nucleosome structure, in which a gene DNA is wound around four core histone octamers. Further, the basic units form a higher-order structure. The neighborhood of the N-terminal of the core histone is in the form of a tail rich in basic amino acids and it further encloses the DNA on the above nucleosome. Lysine residues in the neighborhood of the tail region undergo reversible metabolic turnover of acetylation and are said to be closely involved in the structural control of nucleosome itself or in the transcriptional control through the control of binding with other proteins acting on gene DNA, such as transcriptional factors, silencer proteins and RNA polymerases.

As a demonstration of gene expression control depending on acetylation of histone, it has been reported that higher acetylation of histone promotes the induced expression from genes present in a region of interest while deacetylation forms a transcriptionally inactive region called heterochromatin. That is to say, histone which is a structural protein of chromatin and its acetylation are extended over the whole region of the chromosomal gene; nevertheless, it has been suggested that the function of hi stone greatly affects the expression of a specific gene and, in other words, is involved in the strict control of nuclear signal transmission. An enzyme for acetylating histone is histone acetyltransferase while an enzyme for deacetylating histone is histone deacetylase; these enzymes regulate the kinetic metabolic turnover relating to the level of histone acetylation.

Figure 1:
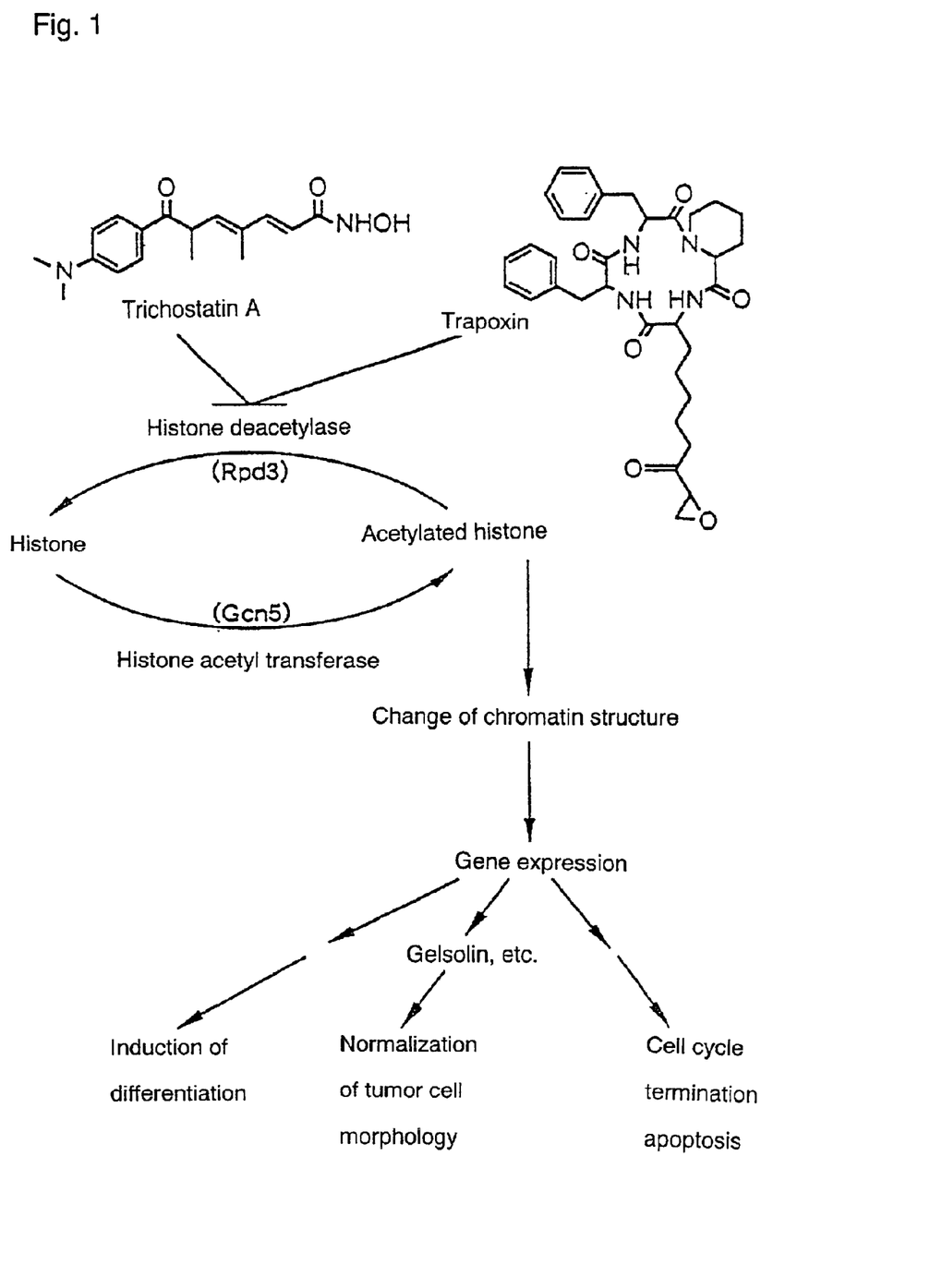
FIG. 1 shows the molecular structures of trichostatin A and trapoxin, as well as one possible action thereof to inhibit histone deacetylation.
Figure 2:
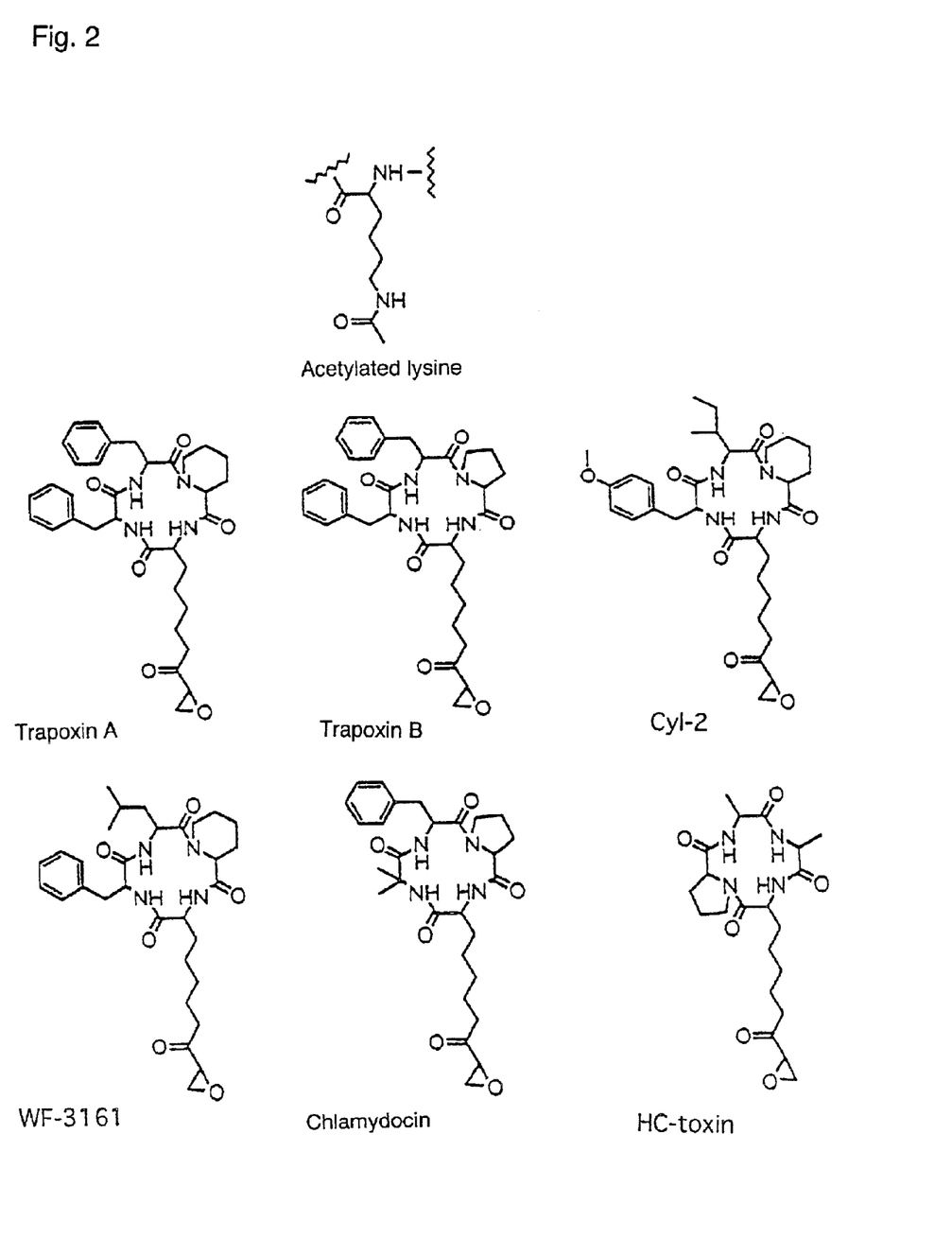
FIG. 2 shows the molecular structures of trapoxin analogs.

If the action of histone deacetylase is enhanced, proper differentiation of cells or normalization of their morphology is inhibited; however, when the enzyme activity of the histone deacetylase is inhibited, the deacetylation from histone is inhibited and, as a result, high acetylation of histone is caused to induce the gene expression required for differentiation and normalization of cell morphology. This phenomenon has been confirmed to some extent by studies using trichostatin A shown in FIG. 1 or trapoxin analogs shown in FIG. 2, which are enzyme inhibitors against histone deacetylase. In addition, when these inhibitors are allowed to act on cells at higher concentrations, cell cycle inhibition is caused and consequently growth inhibition occurs. Trichostatin A exhibits a non-competitive enzyme-inhibiting action at low concentrations and is a reversible inhibitor; on the other hand, trapoxin analogs exhibit competitive inhibitory actions but are irreversible inhibitors. Further, it has also been reported that enzymatically active subunits of human histone deacetylase were purified on an affinity column using K-trap of a cyclic tetrapeptide compound similar to trapoxin; thus, strong evidence has been given to demonstrate that the cyclic tetrapeptide structure as found in trapoxin and the like forms a selective intermolecular linkage with said enzymatically active subunit.

As stated above, since an enzyme inhibitor against histone deacetylase can be a drug causing cell differentiation or normal morphogenesis, it may also exhibit a promotion of the expression of MHC class-I molecule that occurs as a step in the process of differentiation; however, no report confirming this possibility has been made to date. Accordingly, there is a strong need for search and proposal of histone deacetylase enzyme inhibitors that exhibit promoting actions on the expression of MHC class-I molecule in self tissue cells. Further, as stated above, a histone deacetylase enzyme inhibitor at a high concentration causes the inhibition of cell cycle and consequently exhibits growth-inhibiting action, so a need exists for the proposal of a novel anti-cancer agent that is based on the promotion of the MHC class-I molecule expression and which exhibits a combined anti-cancer action due to the contributions of not only the inhibition of tumorization and the elimination of cancer cells by immune system, but also the cell growth-inhibiting action, all being associated with the promotion of MHC class-I molecule expression.

SUMMARY OF THE INVENTION

The present invention provides a novel histone deacetylase enzyme inhibitor exhibiting a promoting action on the expression of MHC class-I molecule in self tissue cells. The present invention also provides a pharmaceutical composition comprising the histone deacetylase enzyme inhibitor of the invention as an active ingredient.

The present invention provides a cyclic tetrapeptide derivative represented by the following general formula (I), (I'), (I") or (I''') or a pharmaceutically acceptable salt thereof:

(I)

(I')

(I")

(I''')

wherein each of $R_{11}$, $R_{12}$, $R_{21}$, and $R_{22}$ independently denotes hydrogen, a linear $C_1$–$C_6$-alkyl group to which a non-aromatic cycloalkyl group or an optionally substituted aromatic ring may be attached, or a branched $C_3$–$C_6$-alkyl group to which a non-aromatic cycloalkyl group or an optionally substituted aromatic ring may be attached; and each of $R_1$, $R_2$ and $R_3$ independently denotes a linear $C_1$–$C_5$-alkylene group which may have a $C_1$–$C_6$ side chain, in which the side chain may form a condensed ring structure on the alkylene chain;

provided that at least one of $R_{11}$, $R_{12}$, $R_{21}$ and $R_{22}$ in general formula (I''') is a cyclohexyl methyl group.

The present invention also provides a histone deacetylase inhibitor and an MHC class-I molecule expression-promoting agent, each comprising the cyclic tetrapeptide derivative or pharmaceutically acceptable salt thereof as an active ingredient.

The invention provides a method of inhibiting a histone deacetylase comprising administering to a subject in need thereof a cyclic tetrapeptide derivative of the invention, or a pharmaceutically acceptable salt thereof, thereby inhibiting a histone deacetylase inhibitor.

The invention provides a method of promoting an expression of an MHC class I molecule comprising administering to a subject in need thereof a cyclic tetrapeptide derivative of the invention, or pharmaceutically acceptable salt thereof, thereby promoting an expression of an MHC class I molecule.

Further, the present invention provides a pharmaceutical composition comprising the cyclic tetrapeptide derivative or pharmaceutically acceptable salt thereof as an active ingredient. In one aspect of the invention, this pharmaceutical composition is used as an anti-cancer agent.

This specification includes part or all of the contents as disclosed in the specification and/or drawings of Japanese Patent Application No. 11-53851, which is a priority document of the present application.

DETAILED DESCRIPTION

The cyclic tetrapeptide derivatives of the present invention are represented by any one of the four mutually related structures shown by general formulae (I) to (I'''). In general formulae (I) to (I'''), each of $R_{11}$, $R_{12}$, $R_{21}$ and $R_{22}$ independently denotes hydrogen, a linear $C_1$–$C_6$-alkyl group to which a non-aromatic cycloalkyl group or an optionally substituted aromatic ring may be attached, or a branched $C_3$–$C_6$-alkyl group to which a non-aromatic cycloalkyl group or an optionally substituted aromatic ring may be attached. Examples of a linear $C_1$–$C_6$-alkyl group and a branched $C_3$–$C_6$-alkyl group may include a methyl group, an ethyl group, a propyl group, a butyl group, a pentyl group, a hexyl group, an isopropyl group, an isobutyl group, a t-butyl group, a sec-pentyl group, a tert-pentyl group, a 1-ethyl-1-methyl-propyl group, and a 1,1-dimethylpropyl group. Examples of a non-aromatic cycloalkyl group include a cyclopropyl group, a cyclobutyl group, a cyclopentyl group, and a cyclohexyl group. Examples of a linear or branched $C_1$–$C_6$-alkyl group to which an optionally substituted aromatic ring is attached include a benzyl group, a 4-methoxybenzyl group, a 3-indolylmethyl group, an (N-methoxy-3-indolyl)methyl group, and a 4-nitrobenzyl group.

In general formulae (I) to (I'''), each of $R_1$, $R_2$ and $R_3$ independently denotes a linear $C_1$–$C_5$-alkylene group that may have a $C_1$–$C_6$ side chain. Examples of a $C_1$–$C_6$ side chain include a methyl group, an ethyl group, a propyl group, a butyl group, a pentyl group, and a hexyl group. The side chain may form a condensed ring structure on the alkylene chain. Examples of an alkylene chain which forms such a condensed ring structure include a 1,2-phenylene group, a 1,3-phenylene group, a 2,3-pyridylene group, a 4,5-pyridinylene group, a 3,4-isoxazonylene group, a 2,4-pyridinylene group, a 3,4-pyridinylene group, a 2,3-pyrazinylene group, a 4,5-pyrimidinylene group, a 3,4-pyridazinylene group, and a 4,5-pyridazinylene group.

The cyclic tetrapeptide derivatives of the present invention and processes for preparing them are described herein. In addition, the pharmacological activities of said cyclic tetrapeptide derivatives are described herein.

First, it will be described that these four molecular structures represented by general formulae (I) to (I''') have mutually close relationship to each other in their structures as stated below and that in this sense, they are compounds having a high degree of structural similarity.

The cyclic tetrapeptide derivative represented by general formula (I) according to the present invention is obtained by first linking the four constituent amino acids to prepare a corresponding chained tetrapeptide derivative and then cyclizing the chained tetrapeptide derivative. Thus, a cyclic tetrapeptide skeleton is formed through peptide linkages of the four α-amino acids represented by the following general formulae (II) to (V), i.e., an α-amino acid represented by general formula (II):

(II)

wherein $R_1$ denotes the same groups as $R_1$ in general formula (I); an α-amino acid represented by general formula (III):

(III)

wherein $R_{21}$ and $R_{22}$ denote the same groups as $R_{21}$ and $R_{22}$ in general formula (I), respectively; a cyclic α-amino acid represented by general formula (IV):

(IV)

wherein $R_3$ denotes the same group as $R_3$ in general formula (I); and an α-amino acid represented by general formula (V):

(V)

and then a hydroxamic acid is derived from the side chain carboxyl group in the above general formula (V).

The cyclic tetrapeptide derivative represented by general formula (I') has an α-amino acid with a cyclic side chain containing an α-carbon atom at a different position from the cyclic tetrapeptide derivative of above general formula (I). Thus, the cyclic tetrapeptide derivative of general formula (I) has an α-amino acid with a cyclic side chain containing an α-carbon atom at a position where the amino acid of general formula (II) is found, while the cyclic tetrapeptide derivative of general formula (I') has an α-amino acid with a cyclic side chain containing an α-carbon atom at a position where the amino acid of general formula (III) is found in general formula (I).

Similarly, the cyclic tetrapeptide derivative represented by general formula (I'') has α-amino acids, each having a cyclic side chain containing an α-carbon atom, at both positions where the amino acids of general formulae (II) and (III) are found in general formula (I).

Further, the derivative represented by general formula (I''') has no α-amino acid with a cyclic side chain containing an α-carbon atom at either position where the amino acid of general formula (II) or (III) is found in general formula (I).

In the cyclic peptide represented by general formula (I) of the present invention, the configuration of their constituent α-amino acids may be either L- or D-configuration; in one aspect, at least one amino acid residue has a different configuration than the other amino acid residues in order to ensure structural stability. Illustratively, at least one or two of the four α-amino acids advantageously has D-configuration while the remainder have L-configuration. When an α-amino acid with a ring structure containing an α-carbon atom has no branch, that is, it is optically inactive, the amino acid of either general formula (III) or (IV) may desirably take D-configuration.

In one aspect of the invention, among the above four amino acids, D-configuration may be chosen for the cyclic amino acid represented by general formula (IV), while the remaining three take L-configuration; or D-configuration may be chosen for the amino acids represented by general formulae (II) and (IV), while the remaining two take L-configuration. It should also be noted that in the cyclic peptide of interest, hydroxamic acid derived from the side chain carboxyl group in the amino acid of general formulae (V) is a site close to the enzymatically active site of histone deacetylase instead of the side chain of N-acetylated lysine, so in one aspect L-configuration is selected for the amino acid of general formulae (V) as in the case of naturally occurring lysine.

The remaining portion of the cyclic tetrapeptide plays such a role that the side chain hydroxamic acid structure derived from the amino acid of the above general formula (V) is directed to the enzymatically active site of histone deacetylase and held there. This role is substantially identical with the function of the cyclic peptide portion of trapoxin analogs that are known irreversible inhibitors. Thus, the remaining portion of the cyclic tetrapeptide provides intermolecular linkage to the neighborhood of the enzymatically active site of histone deacetylase, thereby ensuring that the side chain hydroxamic acid structure derived from the amino acid of the above general formula (V) is fixed onto the enzymatically active site.

Therefore, the remaining three α-amino acids may be of any types so long as their side chains are utilized in binding the peptide to the surface of the histone deacetylase protein. The cyclic amino acid of general formula (IV) is a main functional part for fixing the direction of the side chain hydroxamic acid structure derived from the amino acid of the above general formula (V). In one aspect, the ring structure of the cyclic amino acid of general formula (IV) is a 5-membered ring that is the same as the naturally occurring D-proline in trapoxin B shown in FIG. 2 or a 6-membered ring that is the same as the naturally occurring D-piperidine-2-carboxylic acid in trapoxin A shown in FIG. 2. In alternative aspects, the divalent group $R_3$ constituting this ring is a trimethylene group in proline, a tetramethylene group in piperidine-2-carboxylic acid, or an unsaturated linear hydrocarbon group having a carbon-carbon double bond in correspondence to the linear hydrocarbon group with a chain length of 3 or 4. Alternatively, in these divalent hydrocarbon groups, one or more carbon atoms other than the carbon atom with the free valence which forms a bond to the amino nitrogen atom and the carbon atom at α-position of the carboxylic acid, may be replaced by any heteroatom such as oxygen, sulfur or nitrogen. In alternative aspects, $R_3$ is a trimethylene group or a tetramethylene group.

In alternative aspects of the invention, the remaining two α-amino acids have a side chain as bulky as naturally occurring α-amino acids. That is to say, the side chain should not be more bulky than a p-hydroxybenzyl group of tyrosine, a benzyl group of phenylalanine or a 3-indolylmethyl group of tryptophan in the trapoxin analogs shown in FIG. 2. Exemplary side chain constituents can include leucine, isoleucine, norleucine, cyclohexylalanine, and cyclic aminocarboxylic acids of various ring sizes.

The cyclic tetrapeptide derivative of general formula (I') according to the present invention differs from the cyclic tetrapeptide derivative of general formula (I) only in respect of the position of an α-amino acid with a ring structure containing an α-carbon atom. Therefore, in alternative aspects, amino acids of general formulae (II) to (V), selected for the cyclic tetrapeptide derivative of general formula (I), are also used for the cyclic tetrapeptide derivative of general formula (I'). With respect to the configuration of the amino acids of general formulae (II) to (V), in alternative aspects, a D-configuration is selected for the cyclic α-amino acid of general formula (IV) and the α-amino acid of general formula (II), while the remaining two α-amino acids take L-configuration, and vice versa.

The cyclic tetrapeptide derivative of general formula (I") according to the present invention differs from the cyclic tetrapeptide derivatives of general formula (I) only in that it has an additional α-amino acid with a ring structure containing an α-carbon atom at a position where the amino acid of general formula (III) is found in general formula (I). Therefore, in alternative aspects, amino acids of general formulae (II) to (IV) selected for the cyclic tetrapeptide derivative of general formula (I) are also used for the cyclic tetrapeptide derivative of general formula (I").

The cyclic tetrapeptide derivative of general formula (I'") according to the present invention differs from the cyclic tetrapeptide derivative of general formula (I) only in that the amino acid of general formula (II) in general formula (I) is replaced by an α-amino acid without a ring structure containing an α-carbon atom. Therefore, in alternative aspects, amino acid of general formula (III) selected for the cyclic tetrapeptide derivative of general formula (I) are also used for the cyclic tetrapeptide derivative of general formula (I'").

As stated above, the cyclic tetrapeptide derivative of general formula (I) according to the present invention may be prepared by processes for the formation of peptide chain and cyclization using the four α-amino acids represented by general formulae (II) to (V) as the starting materials. One example of the processes will be generally described below.

Process for Preparation

The cyclic tetrapeptide derivative of the present invention may be prepared by first preparing a chained tetrapeptide intermediate in which the four α-amino acids represented by general formulae (II) to (V) are linked through peptide linkage, then converting it to a cyclic tetrapeptide, and eventually derivatizing the side chain carboxyl group of the α-amino acid represented by general formula (V) to a hydroxamic acid structure. Hereinbelow the process for the preparation will be generally described. The chained tetrapeptide intermediate may be used in a structure which is cleaved at any of the peptide linkages in the desired cyclic tetrapeptide derivative. In the description below, however, a synthesis route via a chained tetrapeptide intermediate having the cyclic α-amino acid represented by general formula (IV) at the C-terminal and the α-amino acid represented by general formula (V) at the N-terminal will be given as an example.

(Step 1) Synthesis of Chained di-, tri- and Tetrapeptides

First, according to a general procedure of peptide synthesis, amino acids of general formulae (III) and (IV) are linked to each other, an amino acid of general formula (II) is then linked, and finally an amino acid of general formula (V) whose side chain carboxyl group has been protected by benzyl esterification is linked to form a chained tetrapeptide.

In this process, Boc-group (t-butoxycarbonyl group) or Z-group (benzyloxycarbonyl group) is used to protect the amino groups of the starting amino acids, t-butyl ester is used to protect the carboxyl groups, and condensation is effected by DCC/HOBt method. The Z-group is removed by catalytic hydrogenolysis with Pd-C catalyst in acetic acid, which is then distilled off, and the free amine is extracted into ethyl acetate using aqueous sodium bicarbonate. An oily product recovered from the extract is used in the subsequent condensation after vacuum drying.

The chained tetrapeptide entirely protected is purified by flash chromatography using a silica gel column.

(Step 2) Synthesis of Cyclic Peptide by Very High Dilution Method

Using trifluoroacetic acid, the Boc-group and t-butyl ester in the chained tetrapeptide entirely protected are removed (deprotected). After distilling off trifluoroacetic acid from the reaction mixture, the product is precipitated with ether and petroleum ether and then vacuum dried.

One-tenth of the amount to be used of the peptide is dissolved in DMF and adjusted to a concentration of 0.1 mM. To the DMF solution under ice cooling, a tertiary amine, e.g., diisopropylethylamine and HATU (0-(7-azabenzotriazol-1-yl)-1,1,3,3-tetramethyluronium hexaflurophosphate) is added, and stirred at room temperature for 30 minutes. Subsequently, 1/10 of the amount to be used of the peptide, diisopropylethylamine and HATU are added to the above DMF solution and stirred at room temperature for 30 minutes. These procedures were repeated 10 times in total to effect a cyclization reaction. After the reaction, the product (cyclic peptide) is extracted into ethyl acetate and then purified by flash chromatography using a silica gel column.

(Step 3) Introduction of Side Chain Hydroxamic Acid Structure

The side chain benzyl ester of the cyclic peptide is removed by catalytic hydrogenolysis with Pd-C catalyst in methanol, and after distilling off methanol, vacuum drying was effected to yield a carboxylic acid as an oily product.

The cyclic peptide compound having a carboxylic acid on the side chain as obtained by the above deprotection and HOBt are dissolved in DMF, and under ice cooling, hydroxylamine hydrochloride, triethylamine and then BOP reagent are added and stirred for 1 hour. After the reaction, DMF was distilled off, decantation is performed with water, and then lyophilization is effected to yield a final product as a white powder. This white powder is dissolved in a small amount of methanol, purified using a semi-preparative column in HPLC, and lyophilized to yield a desired product represented by general formula (I).

The cyclic tetrapeptide derivatives represented by general formula (I'), (I") and (I''') according to the present invention may also be prepared by a similar procedure: first, a chained tetrapeptide is synthesized according to the above Step 1, then converted into a cyclic tetrapeptide utilizing the conditions of Step 2; and the side chain carboxyl group is converted into a side chain hydroxamic acid structure according to Step 3.

In adition to the above synthesis methods, the above compounds may also be synthesized by methods utilizing solid phase synthesis.

A pharmaceutically acceptable salt of the cyclic tetrapeptide derivative according to the present invention means, for example, a salt with a pharmaceutically acceptable inorganic acid, such as hydrochloride, and a salt with a pharmaceutically acceptable organic acid, such as acetate, if the derivative has basic nitrogen atoms.

The MHC class-I molecule expression-promoting agent of the present invention comprises as an active ingredient the cyclic tetrapeptide derivative having a hydroxamic acid structure (hydroxyaminocarbonyl structure) at the side chain terminal as described above, and the agent has an excellent expression-promoting activity as shown in the below-mentioned Test Examples. The MHC class-I molecule expression-promoting action is associated with histone deacetylase enzyme-inhibiting activity and this inhibition is considered to be reversible like trichostatin A having a hydroxamic acid structure. Further, advantages of high therapeutic effects are provided not only by cell growth inhibition and cell cycle-inhibiting action due to histone deacetylase enzyme inhibition which becomes remarkable upon administration at higher concentrations, but also by the complementary effect of action in eliminating cancer cells or cancer virus-infected cells associated with cytotoxic T cells due to promoted MHC class-I molecule expression. In addition, application as a drug is expected, which, when compared with trapoxin analogs which are irreversible inhibitors, allows unfavorable effects on the living body such as side-effects on normal tissue cells persist to a less degree and which, when compared with therapeutic effects, cause greatly reduced relative side-effects. Furthermore, by using the combination of non-aromatic α-amino acids presented herein to construct the cyclic tetrapeptide having a hydroxamic acid side chain, it is expected that the obtained compound will be resistant to attack by a metabolic enzyme, such as cytochrome P-450, and highly stable in vivo.

The invention also provides a method of inhibiting a histone deacetylase by administration of a composition of the invention. Objective tests to determine if a composition (e.g., a cyclic tetrapeptide of the invention) is an effective histone deacetylase inhibitor are well known in the art, see, e.g., Ishiguro (1998) Blood 92:4383–4393; Selker (1998) Proc. Natl. Acad. Sci. USA 95:9430–9435; Warrell (1998) J. Natl. Cancer Inst. 90:1621–1625.

Pharmaceutically acceptable carriers and formulations for peptides and polypeptides are known to the skilled artisan and are described in detail in the scientific and patent literature, see e.g., the latest edition of Remington's Pharmaceutical Science, Maack Publishing Company, Easton, Pa. ("Remington's"); Putney (1998) Nat. Biotechnol. 16:153–157; Patton (1998) Biotechniques 16:141–143; Edwards (1997) Science 276: 1868–1871; U.S. Pat. Nos. 5,780,431; 5,770,700; 5,770,201. The concentration of peptides in formulations of the invention can vary widely, and can be based on fluid volumes, viscosities, body weight and the like in accordance with the particular mode of administration selected and the patient's needs. The pharmaceutical composition may be formulated into any dosage form suitable for its administration route by adding an additive(s) generally used for peptide-like compound formulations of this type to the cyclic tetrapeptide derivative as an active ingredient. In some aspects, the compositions of the invention are high in cell permeability; thus, a variety of administration routes can be used. Dosages, formulations and administration routes and regimens commonly used to administer peptide hormones can be used; see, e.g., U.S. Pat. Nos: 6,211,152; 6,271,196; 6,251,867; 6,245,883; 6,235,712; 6,214,796; 5,935,927.

Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextrans, antioxidants, such as ascorbic acid or glutathione, chelating agents, low molecular weight proteins, compositions that reduce the clearance or hydrolysis of the peptides or polypeptides, or excipients or other stabilizers and/or buffers. Detergents can also used to stabilize or to increase or decrease the absorption of the pharmaceutical composition, including liposomal carriers. Pharmaceutically acceptable carriers and formulations for peptides and polypeptide are known to the skilled artisan and are described in detail in the scientific and patent literature, see e.g., Remington's.

Other physiologically acceptable compounds include wetting agents, emulsifying agents, dispersing agents or preservatives that can preventing the growth or action of microorganisms. Various preservatives are well known and include, e.g., phenol and ascorbic acid. One skilled in the art would appreciate that the choice of a pharmaceutically acceptable carrier including a physiologically acceptable compound depends, for example, on the route of administration of the peptide or polypeptide of the invention and on its particular physio-chemical characteristics.

In one aspect, a solution of peptide or polypeptide of the invention is dissolved in a pharmaceutically acceptable carrier, e.g., an aqueous carrier if the composition is water-soluble. Examples of aqueous solutions that can be used in formulations for enteral, parenteral or transmucosal drug delivery include, e.g., water, saline, phosphate buffered saline, Hank's solution, Ringer's solution, dextrose/saline, glucose solutions and the like; see, e.g., U.S. Pat. Nos. 6,068,850; 5,498,598. The formulations can contain pharmaceutically acceptable auxiliary substances as required to approximate physiological conditions, such as buffering agents, tonicity adjusting agents, wetting agents, detergents and the like. Additives can also include additional active ingredients such as bactericidal agents, or stabilizers. For example, the solution can contain quaternary amine-type preservatives or other disinfectants, osmotic pressure-controlling agents and the like, such as, sodium acetate, sodium lactate, sodium chloride, potassium chloride, calcium chloride, sorbitan monolaurate or triethanolamine oleate; see, e.g., U.S. Pat. No. 5,482,931.

The compositions of the invention can be sterilized by conventional, well-known sterilization techniques, or can be sterile filtered. The resulting aqueous solutions can be packaged for use as is, or lyophilized, the lyophilized preparation being combined with a sterile aqueous solution prior to administration.

Solid formulations can be used for enteral (oral) administration. They can be formulated as, e.g., pills, tablets, powders or capsules. For solid compositions, conventional nontoxic solid carriers can be used which include, e.g., pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10% to 95% of active ingredient (e.g., peptide of the invention). A non-solid formulation can also be used for enteral administration. The carrier can be selected from various oils including those of petroleum, animal, vegetable or synthetic origin, e.g., peanut oil, soybean oil, mineral oil, sesame oil, and the like. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

Peptides and polypeptides of the invention, when administered orally, can be protected from digestion. This can be accomplished either by complexing the peptide or polypeptide with a composition to render it resistant to acidic and enzymatic hydrolysis or by packaging the peptide or complex in an appropriately resistant carrier such as a liposome. Means of protecting compounds from digestion are well known in the art, see, e.g., Fix (1996) Pharm Res. 13:1760–1764; Samanen (1996) J. Pharm. Pharmacol. 48:119–135; U.S. Pat. No. 5,391,377, describing lipid compositions for oral delivery of therapeutic agents.

Systemic administration can also be by transmucosal or transdermal means. For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. See, e.g., Sayani (1996) Crit. Rev. Ther. Drug Carrier Syst. 13:85–184. For topical, transdermal administration, the agents are formulated into ointments, creams, salves, powders and gels. Transdermal delivery systems can also include, e.g., patches.

The peptides and polypeptide complexes can also be administered in sustained delivery or sustained release mechanisms, which can deliver the formulation internally; see, e.g., U.S. Pat. Nos. 5,480,868; 5,187,150. For example, biodegradeable microspheres or capsules or other biodegradable polymer configurations capable of sustained delivery of a peptide can be included in the formulations of the invention; see, e.g., Putney (1998) Nat. Biotechnol. 16:153–157; U.S. Pat. Nos. 6,270,700; 5,635,216; 5,578, 709; 5,445,832.

For inhalation, the peptide or polypeptide can be delivered using any system known in the art, including dry powder aerosols, liquids delivery systems, air jet nebulizers, propellant systems, and the like. See, e.g., Patton (1998) Biotechniques 16:141–143; product and inhalation delivery systems for polypeptide macromolecules by, e.g., Aradigm (Hayward, Calif.), Aerogen (Santa Clara, Calif.), Inhale Therapeutic Systems (San Carlos, Calif.), and the like. For example, the pharmaceutical formulation can be administered in the form of an aerosol or mist. For aerosol administration, the formulation can be supplied in finely divided form along with a surfactant and propellant. In another embodiment, the device for delivering the formulation to respiratory tissue is an inhaler in which the formulation vaporizes. Other liquid delivery systems include, e.g., air jet nebulizers.

In preparing pharmaceuticals of the present invention, a variety of formulation modifications can be used and manipulated to alter pharmacokinetics and biodistribution. A number of methods for altering pharmacokinetics and biodistribution are known to one of ordinary skill in the art. Examples of such methods include protection of the complexes in vesicles composed of substances such as proteins, lipids, for example, liposomes, carbohydrates, or synthetic polymers. For a general discussion of pharmacokinetics, see, e.g., Remington's.

In one aspect, the pharmaceutical formulations comprising peptides or polypeptides of the invention are incorporated in lipid monolayers or bilayers, e.g., liposomes, see, e.g., U.S. Pat. Nos. 6,217,901; 6,110,490; 6,096,716; 6,056, 973; 5,498,598; 5,283,185; 5,279,833. The invention also provides formulations in which water soluble peptides or complexes have been attached to the surface of the monolayer or bilayer. For example, peptides can be attached to hydrazide-, PEG- (distearoylphosphatidyl), ethanolamine-containing liposomes (see, e.g., Zalipsky (1995) Bioconjug. Chem. 6:705:708). Liposomes or any form of lipid membrane, such as planar lipid membranes or the cell membrane of an intact cell, e.g., a red blood cell, can be used. Liposomal formulations can be by any means, including administration intravenously, transdermally (see, e.g., Vutla (1996) J. Pharm. Sci. 85:5–8), transmucosally, or orally. The invention also provides pharmaceutical preparations in which the peptides and/or complexes of the invention are incorporated within micelles and/or liposomes (see, e.g., Suntres (1994) J. Pharm. Pharmacol. 46:23:28; Woodle (1992) Pharm. Res. 9:260–265). Liposomes and liposomal formulations can be prepared according to standard methods and are also well known in the art, see, e.g., Remington's; Akimaru (1995) Cytokines Mol. Ther. 1:197–210; Alving (1995) Immunol. Rev. 145:5–31; Szoka (1980) Ann. Rev. Biophys. Bioeng. 9:467, U.S. Pat. Nos. 4, 235,871, 4,501, 728 and 4,837,028.

The pharmaceutical compositions of the invention can be delivered alone, with excipients or in combination with other pharmaceutical compositions by any means known in the art, e.g., systemically, regionally, or locally; by intraarterial, intrathecal (IT), intravenous (IV), parenteral, intra-pleural cavity, topical, oral, or local administration, as subcutaneous, intra-tracheal (e.g., by aerosol) or transmucosal (e.g., buccal, bladder, vaginal, uterine, rectal, nasal mucosa). Actual methods for delivering compositions will be known or apparent to those skilled in the art and are described in detail in the scientific and patent literature, see e.g., Remington's.

The pharmaceutical compositions can be administered by any protocol and in a variety of unit dosage forms depending upon the method and route and frequency of administration, whether other drugs are being administered, the individual's response, and the like. Dosages for typical nucleic acid, peptide and polypeptide pharmaceutical compositions are well known to those of skill in the art. Such dosages are typically advisorial in nature and are adjusted depending on a variety of factors, e.g., the initial responses (e.g., amount of CTLs generated, tumor shrinkage, and the like), the particular therapeutic context, patient health and tolerance. The amount of pharmaceutical composition adequate to generate the desired response is defined as a "therapeutically effective dose." The dosage schedule and amounts effective for this use, i.e., the "dosing regimen," will depend upon a variety of factors, including, e.g., the diseases or conditions to be treated or prevented by the immunization, the general state of the patient's health, the patient's physical status, age, pharmaceutical formulation and concentration of pharmaceutical composition, and the like. The dosage regimen also takes into consideration pharmacokinetics, i.e., the pharmaceutical composition's rate of absorption, bioavailability, metabolism, clearance, and the like, see, e.g., Remington. Dosages can be determined empirically, e.g., by assessing the abatement or amelioration of symptoms, or, by objective criteria, e.g., measuring levels of antigen-specific CTLs, tumor shrinkage, and the like. While the pharmaceutical compositions of the present invention are not limited by any particular mechanism of action, in one aspect, they attain therapeutic effects by utilizing the above MHC class-I molecule expression-promoting action. Thus, another exemplary method to objectively assess appropriate dosages and efficacy of treatment regimens includes, in addition to measurement of CTL levels and activity and tumor shrinkage or amount of tumor sites, measurement of MHC class I expression.

As noted above, a single or multiple administrations can be administered depending on the dosage and frequency as required and tolerated by the patient. The pharmaceutical compositions can be administered alone or in conjunction with other therapeutic treatments, or, prophylactically. The dose of the cyclic tetrapeptide derivative as an active ingredient may be appropriately determined depending upon the object of the treatment, the degree of symptoms, the sex, age and body weight of a subject to be treated. For example, when an adult male is to be treated, the daily dose can be in the range of 0.1 to 50 mg/kg, 0.5 to 10 mg/kg; in one alternative aspect, this dose is given in multiple sub-doses per day. In one exemplary therapeutic application, compositions of the invention are administered to a patient suffering from a cancer in an amount sufficient to at least partially arrest the disease and/or its complications. For example, in one aspect, a soluble peptide pharmaceutical composition dosage for intravenous (IV) administration would be about 0.01 mg/hr to about 1.0 mg/hr administered over several hours (typically 1, 3, or 6 hours), which can be repeated for weeks with intermittent cycles. Considerably higher dosages (e.g., ranging up to about 10 mg/ml) can be used, particularly when the drug is administered to a secluded site and not into the blood stream, such as into a body cavity or into a lumen of an organ, e.g., the cerebrospinal fluid (CSF).

The invention provides kits that contain the pharmaceutical compositions of the invention, as described above, to practice the methods of the invention. The kit can contain instructional material teaching methodologies, e.g., means to administer the compositions used to practice the invention, means to inject patients or animals with the peptides or polypeptides of the invention, means to monitor the resultant immune response (e.g., CTL response) and assess the reaction of the individual to which the compositions have been administered, and the like.

It will be readily apparent to one skilled in the art that various substitutions and modifications may be made to the invention disclosed herein without departing from the scope and spirit of the invention. It is understood that the examples and aspects described herein are for illustrative purposes only and that various modifications or changes in light thereof will be suggested to persons skilled in the art and are to be included within the spirit and purview of this application and scope of the appended claims.

EXAMPLES

The following examples are offered to illustrate, but not to limit the claimed invention.

The cyclic tetrapeptide derivative of the present invention and processes for the preparation thereof as well as excellent physiological activities of said cyclic tetrapeptide derivative, i.e., excellent MHC class-I molecule expression-promoting action and histone deacetylase enzyme-inhibiting activity, will be described by way of examples.

In the following examples, abbreviations for non-naturally occurring amino acids mean the following amino acid residues:

| | |
|---|---|
| Aib: | 2-aminoisobutyric acid; |
| Asu(NHOH): | 2-amino-7-N-hydroxycarbamoylheptanioic acid; |
| Acc5: | 1-aminocyclopentane-1-carboxylic acid; |
| Acc6: | 1-aminocyclohexane-1-carboxylic acid; |
| Acc7: | 1-aminocycloheptane-1-carboxylic acid; |
| Acc8: | 1-aminocyclooctane-1-carboxylic acid; |
| 1Ain: | 1-aminoindane-1-carboxylic acid; |
| 2Ain: | 2-aminoindane-2-carboxylic acid; |
| Pip: | pipecolic acid; |
| Cha: | cyclohexylalanine. |

Reference Example 1

Synthesis of CHAP-15; cyclo(-L-Asu(NHOH)-Aib-L-Phe-D-Pro-)

CHAP15

Step 1: Z-L-Phe-D-Pro-OtBu

Z-L-Phe-OH (2.25 g, 7.5 mmol) and H-D-Pro-OtBu (0.862 g, 5.0 mmol) were dissolved in DMF (10 ml), mixed with HOBt H₂O (766 mg, 5.0 mmol), BOP (3.3 g, 7.5 mmol) and triethylamine (1.75 ml, 12.5 mmol) under ice cooling, and then stirred for 2 hours. After the reaction mixture was concentrated, it was re-dissolved in ethyl acetate and washed sequentially with 10% citric acid, 4% NaHCO₃ and brine. After drying over anhydrous MgSO₄ and concentrating, the oily residue was purified by flash chromatography on silica gel (CHCl₃/MeOH=99/1) to yield 1.403 g (62%) of the titled compound as an oil.

Rf=0.83 (CHCl₃/MeOH=9/1)

Step 2: H-L-Phe-D-Pro-OtBu

Z-L-Phe-D-Pro-OtBu (1.403 g, 3.1 mmol) was catalytically hydrogenated with Pd-C in acetic acid to remove the Z-group. After the reaction was continued for 10 hours, Pd-C was filtered off and acetic acid was concentrated. The residue was neutralized with 4% NaHCO₃ and extracted into ethyl acetate. The extract was dried over Na₂CO₃ and concentrated to yield 0.853 g (86%) of the titled compound.

Rf=0.50 (CHCl₃/MeOH=9/1)

Step 3: Z-Aib-L-Phe-D-Pro-OtBu

H-L-Phe-D-Pro-OtBu (0.853 g, 2.68 mmol) and Z-Aib-OH (954 mg, 4.02 mmol) were condensed as described in Step 1 above. The oily product was purified by flash chromatography on silica gel (CHCl₃/MeOH=99/1) to yield 1.23 g (85%) of the titled compound.

Rf=0.75 (CHCl₃/MeOH=9/1)

Step 4: H-Aib-L-Phe-D-Pro-OtBu

Z-Aib-L-Phe-D-Pro-OtBu (1.23 g, 2.28 mmol) was catalytically hydrogenated with Pd-C in acetic acid to remove the Z-group. After the reaction was continued for 10 hours, Pd-C was filtered off and acetic acid was concentrated. The residue was neutralized with 4% NaHCO₃ and extracted into ethyl acetate. The extract was dried over Na₂CO₃ and concentrated to yield 0.726 g (1.80 mmol; 79%) of the titled compound.

Rf=0.50 (CHCl₃/MeOH =9/1)

Step 5: Boc-L-Asu(OBzl)-Aib-L-Phe-D-Pro-OtBu

H-Aib-L-Phe-D-Pro-OtBu (0.726 g, 1.80 mmol) and Boc-L-Asu(OBzl)-OH (1.02 g, 2.70 mmol) were condensed as described in Step 1 above. The oily product was purified by flash chromatography on silica gel (CHCl₃/MeOH=49/1) to yield 993 mg (72%) of the titled compound.

Rf=0.71 (CHCl₃/MeOH=9/1)

Step 6: H-L-Asu(OBzl)-Aib-L-Phe-D-Pro-OH.TFA

Trifluoroacetic acid (3 ml) was added to Boc-L-Asu(OBzl)-Aib-L-Phe-D-Pro-OtBu (993 mg, 1.30 mmol) under ice cooling to remove the Boc-group and t-butyl ester at room temperature for 2 hours. After distilling off trifluoroacetic acid, the residue was precipitated with ether/petroleum ether (1:5) and then vacuum dried to yield 737 mg (78%) of the titled compound.

HPLC: Rt=8.66 min (column: Wako pak C4, 4.6×150 mm, 30–100% linear gradient CH₃CN/0.1% TFA over 30 min, flow rate 1.0 ml/min)

Step 7: Cyclo(-L-Asu(OBzl)-Aib-L-Phe-D-Pro-)

H-L-Asu(OBzl)-Aib-L-Phe-D-Pro-OH TFA (30 mg, 0.042 mmol) was dissolved in DMF (400 ml) and adjusted to a concentration of 0.1 mM. To the DMF solution, 10% DIEA/DMF (0.3 ml, 0.17 mmol) and HATU (25 mg, 0.066 mmol) were added and stirred at room temperature for 30 minutes. This procedure was repeated 10 times in total to perform a cyclization reaction. After the reaction, the reaction mixture was concentrated, dissolved in ethyl acetate, and washed sequentially with 10% citric acid, 4% NaHCO₃ and brine. After drying over anhydrous MgSO₄ and concentrating, the oily residue was purified by flash chromatography on silica gel (CHCl₃/MeOH=99/1) to yield 151 mg (61%) of the titled compound.

Rf=0.78 (CHCl₃/MeOH=9/1)

HPLC: Rt=18.15 min (column: MS GEL C18, 4.6×150 mm 30–100% linear gradient CH₃CN/0.1% TFA over 30 min, flow rate 1.0 ml/min)

Step 8: Cyclo(-L-Asu-Aib-L-Phe-D-Pro-)

Cyclo(-L-Asu(OBzl)-Aib-L-Phe-D-Pro-)(151 mg, 0.256 mmol) was dissolved in methanol (5 ml) and catalytically hydrogenated with Pd-C to remove the benzyl ester group. After the reaction was continued for 5 hours, Pd-C was filtered off and methanol was concentrated to yield 124 mg (97%) of the titled compound.

HPLC: Rt=6.32 min (column: Wako pak C4, 4.6×150 mm, 30–100% linear gradient CH₃CN/0.1% TFA over 30 min, flow rate 1.0 ml/min)

Step 9: Cyclo(-L-Asu(NHOH)-Aib-L-Phe-D-Pro-)

Cyclo(-L-Asu-Aib-L-Phe-D-Pro-)(124 mg, 0.248 mmol) was dissolved in DMF (3 ml), and then mixed with hydroxylamine hydrochloride (86 mg, 1.24 mmol), HOBt H₂O (57 mg, 0.372 mmol) and BOP (165 mg, 0.372 mmol) under ice cooling. Triethylamine (0.24 ml, 1.74 mmol) was added and stirred for 2 hours. The reaction mixture was concentrated to 1 ml, and then purified by elution from a LH-20 column (2×85 cm) with DMF. The eluate was lyophilized to yield 95 mg (74%) of the titled compound.

HPLC: Rt=16.32 min (column: Wako pak C18, 4.6×150 mm, 10–100% linear gradient CH₃CN/0.1% TFA over 30 min, flow rate 1.0 ml/min)

FAB-MS: m/z=516 (M+H)+

Example 1
Synthesis of CHAP-54; cyclo(-L-Asu(NHOH)-Acc5-L-Phe-D-Pro-)

This compound was synthesized in accordance with the synthesis method for CHAP-15.

HPLC: Rt=17.04 min (column: MS GEL C18, 4.6×150 mm, 0–100% linear gradient $CH_3CN$/0.1% TFA over 30 min, flow rate 1.0 ml/min)

FAB-MS: m/z=542 (M+H)+

Example 2
Synthesis of CHAP-55; cyclo(-L-Asu(N-HOH)-Acc6-L-Phe-D-Pro-)

This compound was synthesized in accordance with the synthesis method for CHAP-15.

HPLC: Rt=18.25 min (column: MS GEL C18, 4.6×150 mm, 0–100% linear gradient $CH_3CN$/0.1% TFA over 30 min, flow rate 1.0 ml/min)

FAB-MS: m/z=556 (M+H)+

Example 3
Synthesis of CHAP-71; cyclo(-L-Asu(NHOH)-Acc7-L-Phe-D-Pro-)

This compound was synthesized in accordance with the synthesis method for CHAP-15.

HPLC: Rt=19.24 min (column: Wako pak C18, 4.6×150 mm, 0–100% linear gradient $CH_3CN$/0.1% TFA over 30 min, flow rate 1.0 ml/mi)

FAB-MS: m/z=570 (M+H)+

Example 4
Synthesis of CHAP-76; cyclo(-L-Asu(NHOH)-Acc8-L-Phe-D-Pro-)

This compound was synthesized in accordance with the synthesis method for CHAP-15.

HPLC: Rt=18.72 min (column: Wako pak C18, 4.6×150 mm, 0–100% linear gradient $CH_3CN$/0.1% TFA over 30 min, flow rate 1.0 ml/min)

FAB-MS: /z=584 M+H)+

Example 5

Synthesis of CHAP-81; cyclo(-L-Asu(NHOH)-2Ain-L-Phe-D-Pro-)

This compound was synthesized in accordance with the synthesis method for CHAP-15.

HPLC: Rt=18.20 min (column: Wako pak C18, 4.6×150 mm, 0–100% linear gradient $CH_3CN$/0.1% TFA over 30 min, flow rate 1.0 ml/min)

FAB-MS: m/z=590 (N+H)+

Example 6

Synthesis of CHAP-82; cyclo(-L-Asu(NHOH)-1Ain(f)-L-Phe-D-Pro-)

or

This compound was synthesized in accordance with the synthesis method for CHAP-15. 1Ain(f) is 1-aminoindane carboxylic acid as in the case of 1Ain(s) in Example 7. The former is eluted faster than the latter in HPLC, indicating that they are a pair of diastereomers. However, their configurations have not been determined.

HPLC: Rt=16.26 min (column: Wako pak C18, 4.6×150 mm, 0–100% linear gradient $CH_3CN$/0.1% TFA over 30 min, flow rate 1.0 ml/min)

FAB-MS: m/z=590 (M+H)+

Example 7

Synthesis of CHAP-83; cyclo(-L-Asu(NHOH)-1Ain(s)-L-Phe-D-Pro-)

or

-continued

This compound was synthesized in accordance with the synthesis method for CHAP-15.

HPLC: Rt=17.13 min (column: Wako pak C18, 4.6×150 mm, 0–100% linear gradient CH₃CN/0.1% TFA over 30 min, flow rate 1.0 ml/min)

FAB-MS: m/z=590 (M+H)+

Example 8

Synthesis of CHAP-91; cyclo(-L-Asu(NHOH)-2Ain-L-Phe-D-Pip-)

This compound was synthesized in accordance with the synthesis method for CHAP-15.

HPLC: Rt=19.07 min (column: Wako pak C18, 4.6×150 mm, 0–100% linear gradient CH₃CN/0.1% TFA over 30 min, flow rate 1.0 ml/min)

FAB-MS: m/z=604 (M+H)+

Example 9

Synthesis of CHAP-90; cyclo(-L-Asu(NHOH)-Acc8-L-Phe-D-Pip-)

This compound was synthesized in accordance with the synthesis method for CHAP-15.

HPLC: Rt=20.08 min (column: Wako pak C18, 4.6×150 mm, 0–100% linear gradient CH₃CN/0.1% TFA over 30 min, flow rate 1.0 ml/min)

FAB-MS: m/z=598 (M+H)+

Example 10

Synthesis of CHAP-86; cyclo(-L-Asu(NHOH)-D-Cha-L-Ile-D-Pip-) and CHAP-87; cyclo(-L-Asu(NHOH)-D-Cha-L-Ile-L-Pip-)

CHAP86

CHAP87

Step 1: Boc-L-Ile-D,L-Pip-OBzl

Boc-L-Ile-OH ½ H$_2$O (3.92 g, 16.8 mmol), H-D,L-Pip-OBzl HCl (3.57 g, 12 mmol) and HATU (7.75 g, 18 mmol) were dissolved in DMF (15 ml), mixed with Et$_3$N (4.76 ml, 30 mmol) under ice cooling, and then stirred overnight. The reaction mixture was concentrated, extracted with ethyl acetate (120 ml), and washed twice with 10% citric acid, 4% NaHCO$_3$ and then brine, respectively. After drying over magnesium sulfate, ethyl acetate was distilled off. The residue was vacuum dried and purified by flash chromatography (3.5×20 cm) with CHCl$_3$/MeOH (99:1) to yield Boc-L-Ile-D,L-Pip-OBzl (5.90 g, 13.8 mmol; yield 97%) as an oil.

Rf=0.50 (CHCl$_3$/MeOH=49/1)

Step 2: Boc-D-Cha-L-Ile-D,L-Pip-OBzl

Boc-L-Ile-D,L-Pip-OBzl (432 mg, 1 mmol) was dissolved in TFA (3 ml) and allowed to stand for 30 minutes under ice cooling. The reaction solution was distilled and dried under reduced pressure to yield H-L-Ile-D,L-Pip-OBzl TFA (638 mg; yield 144%), which was then dissolved in DMF (5 ml). The solution was mixed with Boc-D-Cha-OH (326 mg, 1.2 mmol) and subsequently mixed with HOBt H$_2$O (230 mg, 1.5 mmol, 1.5 equivalents), Et$_3$N (0.52 ml, 3.7 mmol, 3.7 equivalents) and BOP (663 mg, 1.5 mmol, 1.5 equivalents) under ice cooling, followed by stirring at room temperature for 15 hours. The reaction mixture was concentrated, extracted with ethyl acetate (100 ml), and washed twice with 10% citric acid, 4% NaHCO$_3$ and brine, respectively. After drying over magnesium sulfate, ethyl acetate was distilled off. The residue was vacuum dried and purified by flash chromatography (2.4×14 cm) with CHCl$_3$/MeOH (99:1) to yield Boc-D-Cha-L-Ile-D,L-Pip-OBzl (565 mg, 0.96 mmol; yield 96%) as a foam.

Rf=0.27(CHCl$_3$/MeOH=49/1)

Step 3: Boc-D-Cha-L-Ile-D,L-Pip-OH

Boc-D-Cha-L-Ile-D,L-Pip-OBzl (565 mg, 0.96 mmol) was dissolved in MeOH (10 ml). Pd-C catalyst (250 mg) was added to the solution and the solution was stirred for 15 hours under hydrogen atmosphere to remove the benzyl ester group. After Pd-C catalyst was filtered off, MeOH was distilled off to give a residue, which was then vacuum dried to yield Boc-D-Cha-L-Ile-D,L-Pip-OH (459 mg, 0.93 mmol; yield 97%) as a foam.

Step 4: Boc-D-Cha-L-Ile-D,L-Pip-L-Asu(OBzl)-OTmse

Boc-L-Asu(OBzl)-OTmse (535 mg, 1.1 mmol, 1.2 equivalents) was mixed with TFA (3 ml) under ice cooling and allowed to stand at room temperature for 30 minutes to remove the Boc-group. After distilling off TFA, the reaction mixture was dried under reduced pressure to yield H-L-Asu (OBzl)-OTmse TFA as an oil, which was then dissolved in DMF (5 ml). The solution was mixed with Boc-D-Cha-L-Ile-D,L-Pip-OH (459 mg, 0.93 mmol) and subsequently mixed with HOBt H$_2$O (213 mg, 1.4 mmol, 1.5 equivalents), BOP (616 mg, 1.4 mmol, 1.5 equivalents) and Et$_3$N (0.48 ml, 3.5 mmol, 3.7 equivalents) under ice cooling, followed by stirring at room temperature for 15 hours. The reaction mixture was concentrated, extracted with ethyl acetate (100 ml), and washed twice with 10% citric acid, 4% NaHCO$_3$ and brine, respectively. After drying over magnesium sulfate, ethyl acetate was distilled off. The residue was vacuum dried and purified by flash chromatography (2.4×20 cm) with CHCl$_3$/MeOH (99:1) to yield Boc-D-Cha-L-Ile-D,L-Pip-L-Asu(OBzl)-OTmse (813 mg, 0.93 mmol; yield 100%) as an oil.

Rf=0.20 (CHCl$_3$/MeOH=49/1)

Step 5: H-D-Cha-L-Ile-D,L-Pip-L-Asu(OBzl)-OH TFA

Boc-D-Cha-L-Ile-D,L-Pip-L-Asu(OBzl)-OTmse (813 mg, 0.95 mmol) was dissolved in DMF (2 ml), mixed with a 1M THF solution of tetrabutylammonium fluoride (4 ml, 4 mmol, 4 equivalents), and then allowed to stand at room temperature for 30 minutes. The reaction mixture was concentrated, acidified by addition of 10% citric acid, and then extracted with ethyl acetate (100 ml). The ethyl acetate phase was washed twice with brine, dried over magnesium sulfate, and then distilled to remove ethyl acetate. The residue was vacuum dried to yield Boc-D-Cha-L-Ile-D,L-Pip-L-Asu(OBzl)-OH (696 mg, 0.91 mmol; yeild 97%). Boc-D-Cha-L-Ile-D,L-Pip-L-Asu(OBzl)-OH (696 mg, 0.91 mmol) was mixed with TFA (5 ml) under ice cooling and then allowed to stand at room temperature for 30 minutes to remove the Boc-group. After distilling off TFA, the residue was precipitated with ether/petroleum ether (1:10), filtered and dried under reduced pressure to yield H-D-Cha-L-Ile-D,L-Pip-L-Asu (OBzl)-OH TFA (752 mg, 0.91 mmol; yield 100%).

Step 6: Cyclo(-L-Asu(OBzl)-D-Cha-L-Ile-D,L-Pip-)

H-D-Cha-L-Ile-D,L-Pip-L-Asu(OBzl)-OH TFA (752 mg, 0.91 mmol) was dissolved in DMF (5 ml), 1 ml of which was then transferred to DMF (455 ml, 0.4 mM) and mixed with 1 ml of a solution of HATU (104 mg, 1.5 equivalents) and DIEA (0.63 ml, 4 equivalents) in DMF (10 ml), followed by stirring at room temperature for 1 hour. The same procedure was repeated 5 times to effect a cyclization reaction. The reaction mixture was concentrated, extracted with ethyl acetate (100 ml), and then washed twice with 10% citric acid, 4% NaHCO$_3$ and brine, respectively. After drying over magnesium sulfate, ethyl acetate was distilled off. The residue was vacuum dried and purified by flash chromatography (2.4×40 cm) with CHCl$_3$/MeOH (99:1) to yield cyclo (-L-Asu(OBzl)-D-Cha-L-Ile-D-Pip-) (90 mg, 0.14 mmol;

yield 18%) and cyclo(-L-Asu(OBzl)-D-Cha-L-Ile-D,L-Pip-) (200 mg, 0.31 mmol; yield 40%).

cyclo(-L-Asu(OBzl)-D-Cha-L-Ile-D-Pip-)

Rf=0.45 (CHCl$_3$/MeOH=9/1)

HPLC: Rt=19.40 min (column: Wakosil 5C4, 4.5×150 mm, 37–100% linear gradient CH$_3$CN/0.1% TFA over 30 min)

cyclo(-L-Asu(OBzl)-D-Cha-L-Ile-L-Pip-)

Rf=0.45 (CHCl$_3$/MeOH=9/1)

HPLC: Rt=16.80 min (column: Wakosil 5C4, 4.5×150 mm, 37–100% linear gradient CH$_3$CN/0.1% TFA over 30 min)

Step 7: Cyclo(-L-Asu(OH)-D-Cha-L-fle-D-Pip-) and cyclo (-L-Asu(OH)-D-Cha-L-Ile-D, L-Pip-)

Cyclo(-L-Asu(OBzl)-D-Cha-L-Ile-D-Pip-)(90 mg, 0.14 mmol) and cyclo(-L-Asu(OBzl)-D-Cha-L-Ile-D,L-Pip-) (200 mg, 0.31 mmol) were dissolved in MeOH (5 ml) and MeOH/DMF (1 0:1), respectively. Pd-C catalyst (250 mg) was added to each solution and stirred for 15 hours under a stream of hydrogen to remove the benzyl ester group. After Pd-C catalyst was filtered off, acetic acid was distilled off to give a residue, which was then vacuum dried to yield cyclo(-L-Asu(OH)-D-Cha-L-Ile-D-Pip-)(76 mg, 0.14 mmol; yield 85%) and cyclo(-L-Asu(OH)-D-Cha-L-Ile-D, L-Pip-)(170 mg, 0.31 mmol; yield 99%).

cyclo(-L-Asu(OH)-D-Cha-L-Ile-D-Pip-)

HPLC: Rt=12.64 min (column: Wakosil 5C4, 4.5×150 mm, 37–100% linear gradient CH$_3$CN/0.1% TFA over 30 min)

cyclo(-L-Asu(OH)-D-Cha-L-Ile-L-Pip-)

HPLC: Rt=9.48 min (column: Wakosil 5C4, 4.5×150 mm, 37–100% linear gradient CH$_3$CN/0.1% TFA over 30 min)

Step 8: Cyclo(-L-Asu(NHOH)-D-Cha-L-fle-D-Pip-) and cyclo (-L-Asu(NHOH)-D-Cha-L-Ile-L-Pip-)

Cyclo(-L-Asu(OH)-D-Cha-L-Ile-D-Pip-)(76 mg, 0.14 mmol) and cyclo(-L-Asu (OH)-D-Cha-L-Ile-D,L-Pip-)(170 mg, 0.31 mmol) were dissolved in DMF (3 ml), respectively. Each solution was mixed with HOBt H$_2$O (LDLD compound: 32 mg, 0.21 mmol, 1.5 equivalents; LDLD/LDLL mixture: 71 mg, 0.47 mmol, 1.5 equivalents) and NH$_2$OH HCl (LDLD compound: 49 mg, 0.70 mmol, 5 equivalents; LDLD/LDLL mixture: 108 mg, 1.6 mmol, 5 equivalents), and subsequently mixed with BOP (LDLD compound: 93 mg, 0.21 mmol, 1.5 equivalents; LDLD/LDLL mixture: 206 mg, 0.47 mmol, 1.5 equivalents) and Et$_3$N (LDLD compound: 0.12 ml, 0.84 mmol, 6 equivalents; LDLD/LDLL mixture: 0.20 ml, 1.86 mmol, 6 equivalents) under ice cooling, followed by stirring for 4 hours. After the reaction was completed, the generated Et$_3$N HCl was filtered off and DMF was distilled off. The LDLD compound was purified using a Sephadex LH-20 gel filtration column (2.4×85 cm, DMF), followed by lyophilization, to yield cyclo(-L-Asu (NHOH)-D-Cha-L-Ile-D-Pip-) (20 mg, 0.035 mmol). The LDLD/LDLL mixture was dissolved in a small amount of MeOH and purified by HPLC (column: YMC-Pack C8 10×250 mm, 37% CH$_3$CN/0.1% TFA), followed by lyophilization, to yield cyclo(-L-Asu(NHOH)-D-Cha-L-Ile-D-Pip-)(27 mg, 0.047 mmol; purity 100%) and cyclo(-L-Asu(NHOH)-D-Cha-L-Ile-L-Pip-)(51 mg, 0.090 mmol; purity 93%).

cyclo(-L-Asu(NHOH)-D-Cha-L-Ile-D-Pip-)

HPLC: Rt=21.34 min (column: Wakosil II 5C18, 4.5×150 mm, 10–100% linear gradient CH$_3$CN/0.1% TFA over 30 min)

cyclo(-L-Asu(NHOH)-D-Cha-L-Ile-L-Pip-)

HPLC: Rt=18.79 min (column: Wakosil II 5C18, 4.5×150 mm, 10–100% linear gradient CH$_3$CN/0.1% TFA over 30 min)

FAB-MS (2,2'-dithiodiethanol): m/z=564 [M+H]+

Example 11

Synthesis of CHAP-84; cyclo(-L-Asu(NHOH)-D-Cha-L-Leu-L-Pip-) and CHAP-85; cyclo(-L-Asu(NHOH)-D-Cha-L-Leu-D-Pip-)

CHAP84

CHAP85

The titled cyclic tetrapeptides were synthesized as described in Example 10 (CHAP86, CHAP87), except that BOP reagent (1.5 equivalents) and HOBt H$_2$O (1.5 equivalents) were used for the synthesis of Boc-L-Leu-D,L-Pip-OBzl.

cyclo(-L-Asu(NHOH)-D-Cha-L-Leu-D-Pip-)

HPLC: Rt=20.89 min (column: Wakosil II 5C18, 4.5×150 mm, 10–100% linear gradient CH$_3$CN/0.1% TFA over 30 min)

cyclo(-L-Asu(NHOH)-D-Cha-L-Leu-L-Pip-)

HPLC: Rt=18.33 min (column: Wakosil II 5C18, 4.5×150 mm, 10–100% linear gradient CH$_3$CN/0.1% TFA over 30 min)

FAB-MS (2,2'-dithiodiethanol): m/z=564 [M+H]+

Example 12

Synthesis of CHAP-78; cyclo(-L-Asu(NHOH)-D-Cha-L-Cha-L-Pip-) and CHAP-79; cyclo(-L-Asu(NHOH)-D-Cha-L-Cha-D-Pip-)

CHAP78

CHAP79

The titled cyclic tetrapeptides were synthesized as described in Example 10 (CHAP86, CHAP87), except that DCC (1.3 equivalents) and HOBt H$_2$O (1.3 equivalents) were used for the synthesis of Boc-L-Cha-D,L-Pip-OBzl.

cyclo(-L-Asu(NHOH)-D-Cha-L-Cha-D-Pip-)

HPLC: Rt=26.20 min (column: Wakosil II 5C18, 4.5×150 mm, 10–100% linear gradient CH$_3$CN/0.1% TFA over 30 min)

cyclo(-L-Asu(NHOH)-D-Cha-L-Cha-L-Pip-)

HPLC: Rt=23.36 min (column: Wakosil II 5C18, 4.5×150 mm, 10–100% linear gradient CH$_3$CN/0.1% TFA over 30 min)

FAB-MS (2,2'-dithiodiethanol): m/z=604 [M+H]+

Test Example 1

MHC class-I Molecule Expression-promoting Activity

The cyclic tetrapeptide derivatives of the present invention were investigated for their MHC class-I molecule expression-promoting actions in the following test. Thus, in this test, the cyclic tetrapeptide derivatives of the present invention were allowed to act on cancer cells in order to demonstrated that they promote MHC class-I molecule expression.

Test Method

The cancer cells used were mouse melanoma, B16/BL6 cells, provided by the National Cancer Institute, U.S.A. Said cells were cultured in MEM media supplemented with 10% FBS at 37° C., 5% CO$_2$ in an humidified incubator.

A compound to be tested was preliminarily dissolved in dimethylsulfoxide (DMSO) and adjusted to a concentration of 100 mM or 10 mM (stock solution). A commercially available trichostatin A purchased from Wako Pure Chemical, Japan) which had been proved to have a histone deacetylase enzyme-inhibiting activity, was also dissolved in DMSO and adjusted to a concentration of 5 mg/ml (16.54 mM)(stock solution). Trichostatin A was used as a positive control compound for MHC class-I molecule expression-promoting action due to histone deacetylase enzyme-inhibiting activity. DMSO used as a solvent for the stock solution of a test compound would inevitably be introduced into the medium in the test; however, it had been separately confirmed not to affect the test results in amounts within the range used in the test.

Said B16/BL6 cells were inoculated on a 96-well microplate at a cell density of 5000 cells per well, each well containing 200 $\mu$Al of said medium. After culturing for 24 hours, 10 $\mu$l of a sample containing a given amount of the stock solution of a test compound which had been diluted in the medium was added and cultured for additional 72 hours. Thereafter, each well was washed once with PBS (phosphate buffered saline) and floating cells and the medium were removed. Then, the well was treated with 0.1% glutaraldehyde solution for 3 minutes to fix the cells.

The amount of MHC class-I molecule expressed on the surface of the fixed cells was measured as follows. Anti-H-2K$^b$D$^b$D$^d$ antibody, which is an antibody against mouse MHC class-I molecule (commercially available from Meiji Milk Co., Ltd), was used as a primary antibody, biotinylated anti-mouse IgG+M (commercially available from Chemicon) was used as a secondary antibody, and streptavidin-galactosidase conjugate (commercially available from BRL) was reacted as a labeling enzyme. The amount of the thus labeled enzyme-galactosidase was measured in a microplate reader by recording the fluorescent intensity (excitation: 365 nm, fluorescence: 450 nm) resulting from the enzyme reaction product using 4-methylumbelliferyl-D-galactoside (commercially available from Nacalai Tesque) as a substrate. A fluorescence intensity measured for another well to which no test compound was added and which was treated in a similar manner without adding said primary antibody was used as a background level. The value obtained by subtracting said background level from the actually measured value (an apparent value including the background level) was defined as a true measurement reflecting the amount of expressed MHC class-I molecule.

A group without the addition of any test compound was used as a control group and the measurement of MHC class-I molecule expressed in said group was used as a standard value. The amount of MHC class-I molecule expressed at an addition concentration of each test compound was shown as a relative amount based on said standard value set to one (1). The strength of each test compound activity was compared at a concentration which provides twice-promoted expression ($C_{x2}$).

Part of the results for the cyclic tetrapeptide derivatives of the present invention is shown in Table 1. All the cyclic tetrapeptides shown in Table 1 were demonstrated to have an excellent MHC class-I molecule expression-promoting activity.

TABLE 1

| Test compound | Twice promoting concentration $C_{x2}$ |
| --- | --- |
| CHAP15 | 33.2 nM |
| CHAP54 | 5.67 nM |
| CHAP55 | 5.38 nM |
| CHAP71 | 2.76 nM |
| CHAP76 | 1.88 nM |
| CHAP78 | 2.35 nM |
| CHAP79 | 2.79 nM |
| CHAP81 | 1.29 nM |
| CHAP82 | 2.69 nM |
| CHAP83 | 2.29 nM |
| CHAP84 | 5.65 nM |
| CHAP85 | 2.26 nM |
| CHAP86 | 3.29 nM |
| CHAP87 | 5.39 nM |
| CHAP90 | 3.96 nM |
| CHAP91 | 2.48 nM |

Test Example 2

Inhibitory Activity Against Histone Deacetylase Enzyme

In order to prove that the effects on the cell line in the above Test Example 1 are actually based on the inhibition of histone deacetylase by the cyclic tetrapeptide compounds of the present invention, inhibitory activity against histone deacetylase was examined in an in vitro system as follows.

Test Method

The preparation of histone deacetylase was performed essentially according to the method of Yoshida et al. (J. Biol. Chem., 265, 17174–17179, 1990). The enzyme to be used was partially purified from B16/BL6 cells. The cells were suspended in HDA buffer (15 mM potassium phosphate, 5% glycerol, 0.2 mM EDTA, 1 mM 2-mercaptoethanol, pH 7.5), homogenized and centrifuged (2500× g, 10 min) to collect the nuclei, which were then homogenized in the same buffer containing 1 M $(NH_4)_2SO_4$. After ultrasonic disruption and centrifugation, the concentration of $(NH_4)_2SO_4$ in the collected supernatant was increased to 3.5 M to precipitate histone deacetylase. This precipitate was re-dissolved in HDA buffer, subjected to gel filtration to replace the solvent by HDA buffer, and used as a crude histone deacetylase enzyme solution.

As a substrate, a synthetic substrate peptide, [$^3$H] acetylated histone H4 peptide was used. This [$^3$H]acetylated histone H4 peptide was obtained by synthesizing the N-terminal peptide of histone H4; SGRGKGGKGLGKG-GAKRHRKVC (SEQ ID NO: 1: the C-terminal being cysteine) and then radioactively acetylating with $^3$H-acetic anhydride.

An assay was performed by incubating the synthetic substrate solution and the enzyme solution at 37 for 3 hours in the presence of a compound to be tested (reaction volume, 100 μl). The reaction was stopped by adding 25 μl of 1 M HCl and 0.2 M acetic acid, and [$^3$H]acetate cleaved by the enzyme reaction was extracted with ethyl acetate for radioactivity measurement. For a control group, the same procedure was repeated without addition of any test compound to the reaction system. Each test compound was evaluated for a concentration required to cause 50% inhibition of the histone deacetylase enzyme activity in the control group (50% inhibitory concentration).

Part of the results is shown in Table 2. All the cyclic tetrapeptides shown in Table 2 were demonstrated to have an excellent inhibitory activity against histone deacetylase.

TABLE 2

| Test compound | 50% inhibitory concentration |
| --- | --- |
| CHAP15 | 5.17 nM |
| CHAP54 | 3.02 nM |
| CHAP55 | 2.19 nM |
| CHAP71 | 2.14 nM |
| CHAP76 | 3.99 nM |
| CHAP78 | 3.88 nM |
| CHAP79 | 3.90 nM |
| CHAP81 | 0.980 nM |
| CHAP82 | 1.12 nM |
| CHAP83 | 1.95 nM |
| CHAP84 | 2.22 nM |
| CHAP85 | 1.96 nM |
| CHAP86 | 3.14 nM |
| CHAP87 | 1.98 nM |
| CHAP90 | 2.75 nM |
| CHAP91 | 1.20 nM |

All publications, patents and patent applications cited herein are incorporated herein by reference in their entirety.

INDUSTRIAL APPLICABILITY

The cyclic tetrapeptide derivatives or pharmaceutically acceptable salts thereof according to the present invention have an excellent activity in promoting the MHC class-I molecule expression in association with their excellent inhibitory activity against histone deacetylase enzyme. Further, they also show inhibitory effects on cell proliferation and cell cycle, which are derived from the histone deacetylase inhibition, so that enlargement of cancer tissues is inhibited. Hence, by utilizing the MHC class-I molecule expression-promoting action, they can remarkably promote the elimination of cancer cells by the immune system and are very useful as anti-cancer agents. Since the histone deacetylase inhibition by the cyclic tetrapeptide derivatives of the present invention is reversible, they have the advantage of causing very little unfavorable side effects, such as cell proliferation inhibition and cell cycle inhibition on normal tissues as compared to irreversible inhibitors.

What is claimed is:

1. A cyclic tetrapeptide derivative represented by the following general formula (I), (I'), (I''), (I''') or a pharmaceutically acceptable salt thereof:

(I)

(I')

(I'')

(I''')

wherein each of $R_{11}$, $R_{12}$, $R_{21}$ and $R_{22}$ independently denotes hydrogen, a linear $C_1$–$C_6$-alkyl group to which a non-aromatic cycloalkyl group or an optionally substituted aromatic ring may be attached, or a branched $C_3$–$C_6$-alkyl group to which a non-aromatic cycloalkyl group or an optionally substituted aromatic ring may be attached; and each of $R_1$, $R_2$ and $R_3$ independently denotes a linear $C_1$–$C_5$-alkylene group which may have a $C_1$–$C_6$ side chain, in which the side chain may form a condensed ring structure on the alkylene chain;

provided that at least one of $R_{11}$, $R_{12}$, $R_{21}$ and $R_{22}$ in general formula (I''') is a cyclohexyl methyl group.

2. The cyclic tetrapeptide derivative according to claim 1, represented by said general formula (I), or a pharmaceutically acceptable salt thereof.

3. The cyclic tetrapeptide derivative according to claim 1, represented by said general formula (I'), or a pharmaceutically acceptable salt thereof.

4. The cyclic tetrapeptide derivative according to claim 1, represented by said general formula (I''), or a pharmaceutically acceptable salt thereof.

5. The cyclic tetrapeptide derivative according to claim 1, represented by said general formula (I'''), or a pharmaceutically acceptable salt thereof.

6. A composition comprising pharmaceutical acceptable carrier in combination with the cyclic tetrapeptide derivative according to claim 1.

7. A method of inhibiting a histone deacetylase comprising administering to a subject in need thereof a cyclic tetrapeptide derivative or a pharmaceutically acceptable salt thereof as set forth in claim 1, thereby inhibiting a histone deacetylase.

8. A method of promoting expression of a MHC class I molecule comprising administering to a subject in need thereof a cyclic tetrapeptide derivative or pharmaceutically acceptable salt thereof as set forth in claim 1, thereby promoting expression of a MHC class I molecule.

* * * * *